United States Patent [19]

Perregaard et al.

[11] Patent Number: 5,112,838
[45] Date of Patent: May 12, 1992

[54] METHOD OF TREATING PSYCHOSES IN HUMAN BEINGS WITH THE ATYPICAL NEUROLEPTIC 5-CHLORO-1-(4-FLUOROPHENYL)-3-(1-(2-(2-IMIDAZOLIDINON-1-YL)ETHYL-4-PIPERIDYL)1H-INDOLE

[75] Inventors: Jens Perregaard, Jaegerspris; Torben Skarsfeldt, Broendby Strand, both of Denmark

[73] Assignee: H. Lundbeck A/S, Denmark

[21] Appl. No.: 508,240

[22] Filed: Apr. 11, 1990

[30] Foreign Application Priority Data

Apr. 11, 1989 [GB] United Kingdom ............... 8908085

[51] Int. Cl.⁵ .................................... A61K 31/445
[52] U.S. Cl. ............................................. 514/323
[58] Field of Search ........................... 514/323, 339

[56] References Cited

U.S. PATENT DOCUMENTS

| | | | |
|---|---|---|---|
| 4,359,468 | 11/1982 | Freter et al. | 514/322 |
| 4,710,500 | 12/1987 | Perregaard | 514/254 |
| 4,742,057 | 5/1988 | Ueda et al. | 514/235 |

OTHER PUBLICATIONS

Skarsfeldt, T et al., Eur. J. Pharmacol. 182:613-14 (1990).
"Current CNS Patents", vol. 1, No. 10, for Dec. 1990—eight (8) pages including especially pp. 653 and 654 relating to Sertindole, a highly selective atypical neuroleptic.
"The Positive-Negative Dimension in Schizophrenia: Its Validity and Sifnificance", Psychiatric Developments 2, pp. 79-103; Stanley R. Kay and Lewis A. Opler; Oxford University Press (1987).

Primary Examiner—Glennon H. Hollrah
Assistant Examiner—Gary E. Hollinden
Attorney, Agent, or Firm—Dressler, Goldsmith, Shore, Sutker & Milnamow, Ltd.

[57] ABSTRACT

A method of treating psychoses in human beings with the atypical neuroleptic 5-chloro-1-(4-fluorophenyl)-3-(1-(2-(2-imidazolidinon-1-yl) ethyl-4-piperidyl)-1H-indole, having the formula:

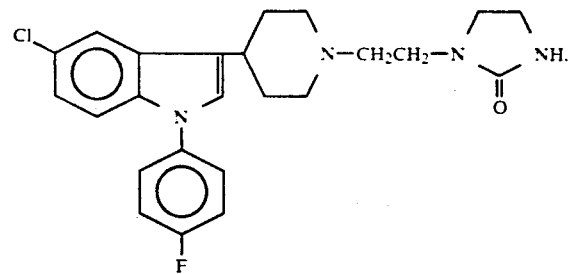

or a pharmaceutically-acceptable salt thereof, thereby to selectively block dopamine neurones in the ventral tegmental area of the brain, substantially without blocking dopamine neurones in the substantia nigra pars compacta, and therefore without the usual extrapyramidal side effects of common neuroleptics, is disclosed.

3 Claims, No Drawings

METHOD OF TREATING PSYCHOSES IN HUMAN BEINGS WITH THE ATYPICAL NEUROLEPTIC 5-CHLORO-1-(4-FLUOROPHENYL)-3-(1-(2-(2-IMIDAZOLIDINON-1-YL)ETHYL-4-PIPERIDYL)1H-INDOLE

FIELD OF THE INVENTION

The present invention relates to a new method for the treatment of mental disorders, especially psychoses, and to a specific compound for use in this new method.

BACKGROUND OF THE INVENTION

Damping of dopamine (DA) overactivity by the use of DA-receptor blocking drugs is today the most important principle in the treatment of schizophrenia. "Classical neuroleptics" such as haloperidol, cis(Z)-flupentixol or chlorpromazine induce antipsychotic effect via DA-receptor blockade. Pharmacologically, such compounds antagonize stereotypies induced by dopaminergic compounds (i.e. methylphenidate, apomorphine, amphetamine) in mice or rats. Unfortunately, the incidence of severe extrapyramidal side effects (EPS) (dystonia, akathisia and parkinsonism) is very frequent in long term treatment with these neuroleptics and causes great concern among clinicians. The EPS are difficult to treat, and unsuccessful treatment often leads to poor medication compliance. Some of these neurological side effects, which generally involve involuntary movement disorders, have been correlated to the propensity of the drugs to induce catalepsy in rats (Arnt. et al., Neuropharmacology 20, 1331–1334 (1981)).

A class of compounds, which does not produce EPS and which is effective in the treatment of schizophrenic disorders, is termed "atypical neuroleptics". Clozapine is the prototype of such drugs. Clozapine is an effective antipsychotic in man but, due to severe incidences of agranulocytosis it is rarely used clinically. Pharmacologically clozapine induces no catalepsy in rats, neither does it inhibit stereotypies induced by dopaminergic agonists in rodents. Clozapine blocks central serotonergic and noradrenergic receptors in animal studies.

In recent years several reports have suggested that inhibition of the spontaneous firing activity of DA neurones in ventral tegmental area (VTA) in the rat brain upon repeated treatment with a neuroleptic is indicative of the antipsychotic potential of the compound, whereas inhibition of the activity in substantia nigra pars compacta (SNC) should account for the development of EPS (Bunney and Grace, Life Science 25, 1715–1725 (1978), White and Wang, Science 221, 1054–1057 (1983), Chiodo and Bunney, J. Neuroscience 5, 2539–2544 (1985), Skarsfeldt, Life Science 42, 1037–1044 (1988)). "Classical neuroleptics" are active in both areas in the same dose range while "atypical neuroleptics" mainly inactivate DA neurons in the VTA area. Clozapine has been shown to be active only in the VTA area.

U.S. Pat. No. 4,710,500 discloses a class of optionally 5-substituted 1-aryl-3-piperidinyl-, 1-aryl-3-1,2,3,6-tetrahydropyridinyl or 1-aryl-3-piperazinyl-indol derivatives having potent dopamine antagonist activity in vivo and in vitro, as tested in pharmacological tests. The tests used were methylphenidate antagonism, catalepsy and $^3$H-spiroperidol binding tests. Accordingly, the compounds of U.S. Pat. No. 4,710,500 have been shown having "Classically neuroleptic activity".

SUMMARY OF THE INVENTION

Surprisingly, it has now been found that the compound 5-chloro-1-(4-fluorophenyl)-3-(1-(2-(2-imidazolidinon-1-yl)ethyl)-4-piperidyl)-1H-indole. (Lu23-174) known from said U.S. Patent, as well as salts thereof, selectively block the spontaneously active DA-neurones in VTA areas in rats. The selectivity is over a wide range of dose, and only at very high dose levels the active DA-neurones are also blocked in SNC areas (Table 1). This effect is outstanding and unique for this compound compared to the effects of other phenylindoles disclosed in U.S. Pat. No. 4,710,500. Close analogues, such as 1-(4-fluorophenyl)-3-(4-(3-hydroxypropyl)-1-piperazino)-5-trifluoromethyl-1H-indole (Lu 24-143), inhibit the activity equipotently in both SNC and VTA areas or are inactive such as 1-(4-fluorophenyl)-3-(1-(2-(2-imidazolidinon-1-yl)ethyl)-4-piperidyl)-1H-indole, (Lu 23-086) (Table 1).

As reported for clozapine, the 5-chloro-1-(4-fluorophenyl)-3-(1-(2-(2-imidazolidinon-1-yl)ethyl)-4-piperidyl)-1H-indole, does not block dopaminergic stereotypies such as methylphenidate-induced gnawing in mice or stereotyped movements of head and forelegs in rats provoked by the administration of amphetamine (Table 2). The compound is non-cataleptic even at very high doses (Table 2).

According to the classical tests for neuroleptic activity (i.e. catalepsy and blocking of dopaminergic stereotypies) as provided in U.S. Pat. No. 4,710,500, the compound of the present invention appears relatively inactive. However, it has now been proven to have unique "atypically neuroleptic" profile and has been demonstrated to be a very promising drug for the treatment of schizophrenia and related psychic disorders.

Centrally acting serotonin 5-HT$_2$ antagonists are able to block the characteristic rapid shake (twitch) of the head in rats induced by administration of the 5-HT$_2$ agonist quipazine. 5-chloro-1-(4-fluorophenyl)-3-(1-(2-(2-imidazolidinon-1-yl)ethyl)-4-piperidyl)-1H-indole has a very potent and long-acting inhibitory activity against such quipazine-induced head twitches (Table 2). The potent central 5-HT$_2$ antagonistic effect may suggest that the compound additionally shows effectiveness on negative symptoms in schizophrenic patients, and improvement of the quality of sleep. (Janssen P. A. J, 1988, Pharmacopsychiat. 21, 33–37).

Accordingly, the present invention provides a method of treating psychosis in humans, substantially without producing any extrapyramidal side effects, comprising the step of administering an effective amount of the atypical neuroleptic, 5-chloro-1-(4-fluorophenyl)-3-(1-(2-(2-imidazolidinon-1-yl)ethyl)-4-piperidyl)-1H-indole,

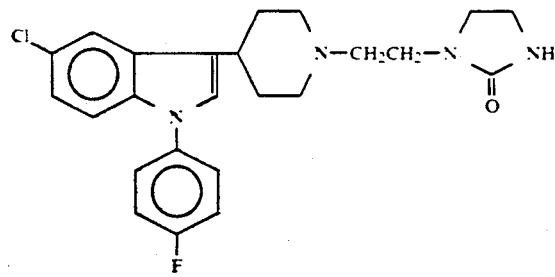

or a pharmaceutically acceptable acid addition salt thereof, to a patient in need thereof.

The term "atypical neuroleptic" is used through this specification and claims in the meaning: selectively blocking the DA-neurones in the ventral tegmental area (VTA), or in the limbic areas, and substantially without activity in substantia nigra pars compacta (SNC).

The term "block the dopamine neurones" is through this specification with claims intended to mean reducing or decreasing the number of spontaneously active dopamine neurones, or substantially inactivating all such neurones.

An effective amount of the present substance in the method of the invention is from 0.0001 to 1.0 mg/kg daily. Preferably, the daily dose is administered in one or more unit doses and, accordingly, a preferred unit dose will be from 0.001 to 7.0 mg.

In another aspect the present invention provides a method of treating negative symptoms of schizophrenia in human beings, comprising the step of administering an effective amount of 5-chloro-1-(4-fluorophenyl)-3-(1-(2-(2-imidazolidinon-1-yl)ethyl)-4-piperidyl)-1H-indole or a pharmaceutically acceptable salt thereof to a patient in need thereof.

In a further aspect, the present invention provides a method for the improvement of the quality of sleep in a schizophrenic patient, comprising the step of administering an effective amount of 5-chloro-1-(4-fluorophenyl)-3-(1-(2-(2-imidazolidinon-1-yl)ethyl)-4-piperidyl)-1H-indole or a pharmaceutically acceptable salt thereof.

The compound of the present invention, 5-chloro-1-(4-fluorophenyl)-3-(1-(2-(2-imidazolidinon-1-yl)ethyl-4-piperidyl)-1H-indole, is also designated sertindole (a recommmmmded INN name), and in the following this INN name will be used for short.

Sertindole may be synthesized as disclosed in U.S. Pat. No. 4,710,500. The pharmaceutically acceptable acid addition salts of the compound may be formed with non-toxic organic or inorganic acids in an aqueous miscible solvent, such as acetone or ethanol, with isolation of the salt by concentration and cooling or an excess of the acid in aqueous immiscible solvent, such as ethyl ether or chloroform, with the desired salt separating directly.

Exemplary of such organic salts are those with maleic, fumaric, benzoic, ascorbic, embonic, succinic, oxalic, bis methylene-salicylic, methanesulfonic, ethanedisulfonic, acetic, propionic, tartaric, salicylic, citric, glucomic, lactic, malic, mandelic, cinnamic, citraconic, aspartic, stearic, palmitic, itaconic, glycolic, p-aminobenzoic, glutamic, benzene sulfonic and theophylline acetic acids as well as the 8-halotheophyllines, for example 8-bromo-theophylline. Exemplary of such inorganic salts are those with hydrochloric, hydrobromic, sulfuric, sulfamic, phosphoric and nitric acids. Of course, these salts may also be prepared by the classical method of double decomposition of appropriate salts, which is wellknown to the art.

Sertindole and the pharmaceutically acceptable acid addition salts thereof, may be administered both orally and parenterally, for example in the form of tablets, capsules, powders, syrups or solutions for injection.

PHARMACOLOGICAL TEST METHODS

Sertindole and reference compounds were tested according to reliable and well-known pharmacological methods as follows:

1) Inhibition of DA cell firing in VTA and SNC areas

This test model is used to examine the effects on spontaneously active DA neurones in ventral tegmental area (VTA) and substantia nigra pars compacta (SNC) upon repeated oral treatment. Inhibition of the number of active DA neurones in VTA indicates an antipsychotic effect of a compound, while inhibition of the number of active DA neurones in SNC accounts for the development of neurological side effects.

For further information see Skarsfeldt (1988) which information is incorporated herein by reference.

Rats weighing 250 g at the start of the experiment are used. After 21 days of oral treatment with different doses of test compound the rats are anaesthetized and mounted in a stereotaxic instrument. A hole (3×3 mm) is drilled in the skull. Recording of DA neurone activity is performed with a single barrel glass electrode. Eight electrode penetrations are made through VTA and SNC.

The data are expressed as per cent inhibition of the activity in non-treated animals.

$ED_{50}$ values were calculated by log-probit analysis.

Ref.: Skarsfeldt, T.: Eur. J. Pharmacol. 145, 239–243 (1988).

2) Methylphenidate antagonism

The inhibiting effect of test substances on the methylphenidate-induced gnawing in mice is determined as described by Pedersen and Christensen (1972). The test substance is given s.c. in different doses while methylphenidate is given s.c. in the dose of 60 mg/kg 2 hours after injection of test substance. 3×2 mice (18–25 grams) are used per dose of the test substance. The results are given in fractions: 0/3, ⅓, ⅔ and 3/3, where 0, 1, 2 and 3 are the number of pairs which has not been gnawing on receipt of the test substance. $ED_{50}$ values were calculated by log-probit analyses and are expressed as μmol/kg, s.c.

Ref: Pedersen, V. and Christensen, A. V.: Acta pharmacol. et toxicol. 31, 488-496, 1972.

3) Amphetamine antagonism

The inihibting effect of test substances on the amphetamine-induced stereotyped movements of head and forelegs in rats is determined as described by Møller Nielsen et al. (1973).

The test substance is given s.c. in different doses, while amphetamine is given s.c. in the dose of 10 mg/kg 2 hours after the injection of test substance. Five rats (230–270 g) are used for each dose of test substance. The results are stated in fractions: 0/3, ⅓, ⅔ and 3/3, where 0, 1, 2 and 3 are the number of rats which has not shown stereotypies on receipt of test substance. $ED_{50}$ values were calculated by log-probit analyses and are expressed as μmol/kg. s.c.

Ref.: Møller Nielsen. I. et al.: Acta Pharmacol. et Toxicol. 33, 353-362, 1973.

4) Catalepsy

This effect is used to evaluate the ability of a compound to induce extra-pyramidal side effects. Evaluation of catalepsy is made according to Arnt (1983). Test compound is given s.c. in different doses. The rat (170-240 g) is placed on a vertical wire mesh (mesh diameter 12 mm). The rat is considered cataleptic if it remains immobile for more than 15 seconds. The maximum number of rats showing catalepsy within the first 6 hours is recorded for each dose group. The results are recorded in fractions, and an $ED_{50}$ value is calculated by means of log-probit analysis.

Ref.: Arnt, J.: Eur. J. Pharmacol. 90, 47-55 (1983).

5) Quipazine antagonism

The test compound or saline is injected subcutaneously 2 hours or 24 hours before s.c. injection of quipazine hemimaleate (6.8 mg/kg). At least 3 dose groups, each consisting of at least 4 rats, are used. The rats are individually placed in observation cages (12×25 cm). The number of head twitches is counted 30-40 minutes after quipazine administration. Inhibition of head twitches is expressed in per cent of the number of head twitches in the control group. $ED_{50}$ values are calculated by log-probit analysis.

Ref.: Arnt, J. et al: Drug Development Research. 1989, 16, 59-70.

the classical neuroleptics haloperidol and cis(Z)-flupentixol. Furthermore it is seen that sertindole is far more selective and more potent than the reference compound clozapine.

From Table 2 it will appear that sertindole is relatively inactive in the classical neuroleptic tests and, therefore, is expected to be substantially without the EPS.

Additionally, sertindole is showing potent and long lasting quipazine inhibition and, accordingly, $5HT_2$ antagonistic activity.

In Vivo Activity in Rats

The "atypical neuroleptic" profile of sertindole has been established in an in vivo dopamine infusion model in rats (see B. Costall et al., Br. J. Pharmacol. 90. p. 89 (1987) and B. Costall et al., Reviews in the Neurosciences 2 (1), 41-65 (1988) for a detailed description of this animal model).

Administration of sertindole in an amount of 0.0025-1.25 mg/kg/day (s.c.) significantly reduced the locomotor hyperactivity induced by bilaterally infused dopamine in the nucleus accumbens. No "rebound" hyperactivity was found after termination of the sertindole treatment. On the other hand, termination of treatment with classical neuroleptics such as fluphenazine results in a marked and persistent increase of locomotor activity.

Typical examples of formulas for composition containing sertindole or an pharmaceutically acceptable acid addition salt thereof as an active ingredient, are as follows:

TABLE 1

Inhibition of firing rate of DA neurones after repeated treatment (21 days).

| Compound | VTA area $ED_{50}(μmol/kg/day)$ (po) | SNC area $ED_{50}(μmol/kg/day)$ (po) | SNC/VTA ratio |
|---|---|---|---|
| sertindole | 0.015 | 1.6 | 107 |
| Lu 24-143 | 0.048 | 0.033 | 0.7 |
| Lu 23-086 | >12 | >12 | |
| clozapine | 56 | >120 | >2.2 |
| haloperidol | 0.043 | 0.033 | 0.8 |
| cis(Z)-flupentixol | 0.037 | 0.044 | 1.2 |

TABLE 2

Effects of different neuroleptics on methylphenidate-induced gnawing (MePh. antg.) in mice, amphetamine-induced stereotypies (Amph. antg.) in rats, cataleptic effect in rats and inhibition of quipazine-induced head twitches in rats (2 and 24 hours after drug treatment). $ED_{50}$ values were calculated by log-probit analyses and are expressed as μmol/kg. sc.

| Compound | MePh. antg. $ED_{50}(μmol/kg)(sc)$ | Amph. antg. $ED_{50}(μmol/kg)(sc)$ | Catalepsy $ED_{50}(μmol/kg)(sc)$ | Quipazine inhibition $ED_{50}(μmol/kg)(sc)$ 2 hrs | 24 hrs |
|---|---|---|---|---|---|
| sertindole | >180 | >45 | >91 | 0.04 | 0.03 |
| Lu 24-143 | 0.08 | 0.02 | 0.07 | 0.005 | 0.22 |
| Lu 23-086 | >98 | NT* | >98 | 0.04 | 0.08 |
| clozapine | >120 | >120 | >120 | 1.1 | >7.6 |
| chlorpromazine | 5.1 | 20 (ip) | 19 | 0.37 | NT |
| haloperidol | 0.19 | 0.15 | 0.33 | 0.99 | NT |
| cis(Z)-flupentixol | 0.10 | 0.06 | 0.16 | 0.04 | >4.9 |

*NT: Not tested

It appears from Table 1 that sertindole has a very high SNC/VTA ratio and thus is very selectively blocking the DA-neurones in the VTA area as compared to the most closely related compounds of U.S. Pat. No. 4,710,500, 1-(4-fluorophenyl)-3-(4-(3-hydroxypropyl)-1-piperazino)-5-trifluoromethyl-1H-indole (Lu 24-143) and 1-(4-fluorophenyl)-3-(1-(2-(2-imidazolidinon-1-yl)ethyl-4-piperidyl)-1H-indole (Lu 23-086) and 1) Tablets containing 0.5 milligrams of sertindole calculated as the free base:
Sertindole: 0.5 mg
Lactose: 18 mg
Potato starch: 27 mg
Saccharose: 58 mg
Sorbitol: 3 mg Talcum: 5 mg
Gelatine: 2 mg
Povidone: 1 mg
Magnesium stearate: 0.5 mg
2) Tablets containing 5.0 milligrams of sertindole calculated as the free base:
Sertindole: 5.0 mg
Lactose: 16 mg
Potato starch: 45 mg
Saccharose: 106 mg
Sorbitol: 6 mg
Talcum: 9 mg
Gelatine: 4 mg
Povidone: 3 mg
Magnesium stearate: 0.6 mg
3) Syrup containing per milliliter:
Sertindole: 1.0 mg
Sorbitol: 500 mg
Tragacanth: 7 mg
Glycerol: 50 mg
Methyl-paraben: 1 mg
Propyl-paraben: 0.1 mg
Ethanol: 0.005 ml
Water: ad 1 ml
4) Solution for injection containing per milliliter:
Sertindole: 2 mg
Acetic acid: 17.9 mg
Sterile water: ad 1 ml
5) Solution for injection containing per milliliter:
Sertindole: 0.10 mg
Sorbitol: 42.9 mg
Acetic acid: 0.63 mg
Sodium hydroxide: 22 mg
Sterile water: ad 1 ml Any other pharmaceutical tableting adjuvants may be used provided that they are compatible with the active ingredient, and additional compositions and dosage forms may be similar to those presently used for neuroleptics, such as clopenthixol, flupentixol or fluphenazine.

Also combinations of the compounds of Formula I as well as their non-toxic acid salts with other active ingredients, especially other neuroleptics, thymoleptics, tranquilizers, analgetics or the like, fall within the scope of the present invention.

It is to be understood that the invention is not limited to the exact details of operation or exact compound or compositions shown and described, as obvious modifications and equivalents will be apparent to one skilled in the art.

We claim:

1. A method of treating positive symptoms of schizophrenia in humans comprising the step of administering a therapeutically effective amount of the compound:

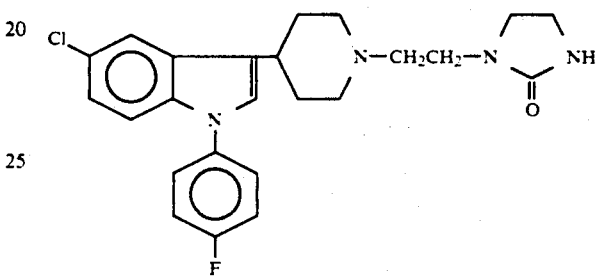

or a pharmaceutically acceptable acid addition salt thereof, to a patient in need thereof.

2. A method as claimed in claim 1 wherein the compound is administered in the form of a unit dose.

3. A method as claimed in claim 2 wherein the unit dose contains 0.001 to 7.0 mg of the compound.

* * * * *